United States Patent [19]

Mumallah et al.

[11] Patent Number: 4,644,073

[45] Date of Patent: Feb. 17, 1987

[54] PERMEABILITY CONTRAST CORRECTION EMPLOYING A SULFATE-FREE PROPIONATE-SEQUESTERED CHROMIUM (III) SOLUTION

[75] Inventors: Naim A. Mumallah; Tod K. Shioyama, both of Bartlesville, Okla.

[73] Assignee: Phillips Petroleum Company, Bartlesville, Okla.

[21] Appl. No.: 710,754

[22] Filed: Mar. 11, 1985

[51] Int. Cl.$^4$ ............................................. C07F 11/00
[52] U.S. Cl. ............................................. 556/2; 556/5; 556/6; 556/61; 556/4; 252/8.554
[58] Field of Search ........................... 556/2, 4, 5, 6, 61

[56] References Cited

U.S. PATENT DOCUMENTS

| | | | |
|---|---|---|---|
| 2,470,378 | 5/1949 | Skala | 556/61 X |
| 2,615,031 | 10/1952 | Stover. | |
| 2,650,239 | 8/1953 | Stover. | |
| 2,678,328 | 5/1954 | Drew. | |
| 3,193,398 | 7/1965 | Iannicelli. | |
| 3,256,266 | 6/1966 | Burt. | |
| 3,462,496 | 8/1969 | Fletcher et al. | |
| 3,705,183 | 12/1972 | Bunger et al. | 556/61 X |
| 3,714,211 | 1/1973 | Erdmann et al. | |
| 3,845,822 | 11/1974 | Clampitt et al. | |
| 3,900,689 | 8/1975 | Deyrup. | |
| 3,926,258 | 12/1975 | Hessert et al. | |
| 3,932,285 | 1/1976 | Ceprini et al. | 556/61 X |
| 3,959,093 | 5/1976 | Merkl. | |
| 4,488,601 | 12/1984 | Hammett. | |

OTHER PUBLICATIONS

Chemical Abstracts, vol. 66, 25561j, (1967).
Chemical Abstracts, vol. 83, 169154c, (1975).
Chemical Abstracts, vol. 97, 151613f, (1982).
Chemical Abstracts, vol. 73, 70366e, (1970).
Chemical Abstracts, vol. 95, 139641q, (1981).
Chemical Abstracts, vol. 87, 142053q, (1977).
Chemical Abstracts, 74, 23649k, (1971).
Yost et al, *Systematic Inorganic Chemistry of the Fifth and Sixth Group Nonmetallic Elements*, Prentice-Hall, (N.Y., 1946), p. 326.

*Primary Examiner*—Helen M. S. Sneed
*Attorney, Agent, or Firm*—French and Doescher

[57] ABSTRACT

A sulfate-free clear green solution of chromium(III) propionate is prepared by mixing aqueous propionic acid containing up to 55 weight percent propionic acid with a chromium(VI) oxidant, such as a dichromate or chromate, and a sulfur-containing reductant, such as a bisulfite, which on reacting yields two phases: a lower sulfate-containing phase for discard or recycle and an upper phase solution of sulfate-free clear green propionate-sequestered chromium(III), the latter phase being stabilized with additional acid. The upper phase solution is useful for crosslinking polymeric viscosifiers such as partially hydrolyzed acrylamide-based polymers and the like in permeability contrast corrections in enhanced oil recovery operations.

20 Claims, 2 Drawing Figures

1

PERMEABILITY CONTRAST CORRECTION EMPLOYING A SULFATE-FREE PROPIONATE-SEQUESTERED CHROMIUM (III) SOLUTION

FIELD OF THE INVENTION

The invention pertains to methods of preparing stable aqueous sulfate-free propionate-sequestered chromium-(III) solutions. In a particular aspect, the invention pertains to the use of inorganic sulfur compound/chromium(VI) redox system to prepare aqueous sulfate-free propionate-sequestered chromium(III) solutions. The invention further pertains to methods for correcting the water permeability contrast of heterogeneous subterranean formations.

BACKGROUND OF THE INVENTION

In oil-producing fields employing waterflooding, the water tends to channel through zones of high permeability and to by-pass a large amount of oil-in-place. Since waterflooding fluids usually contain chemicals, and even relatively small amounts of chemicals in the hundreds of millions of gallons of water employed become expensive, an efficient sweep by the waterflood is important.

Water channeling can be reduced by injecting a solution of a polymer and a polyvalent metal cation cross-linking agent under conditions which gel the polymer, plugging off the more permeable zones, and diverting the subsequently injected water into the formerly less permeable but now relatively more permeable oil-bearing strata. The use of such as aluminum citrate and related polyvalent metal cations as crosslinking agents has been known for some time. However, citrate-sequestered aluminum type of agents has not been entirely satisfactory in some of the more hostile environments, such as formation temperatures of greater than about 170° F. and/or hardness cation values in the formation water of greater than about 500 ppm.

Chromium(III) propionate solution is an effective agent for crosslinking polymers such as the partially hydrolyzed acrylamide-based polymers to form a gel in high permeability zones of an oil bearing reservoir, in either near-well treatments or indepth applications. Not only is chromium(III) propionate solution effective for such permeability correction processes, and is useful in hard brines, but that, surprisingly, the propionate component is biocidal against the pestiferous sulfate-reducing bacteria usually present in the formation water. Thus, both the crosslinking benefits can be obtained, plus the biocidal benefits.

However, preparation of useful chromium propionate solutions has proven difficult. The chromium(III) propionate solution must be discretely prepared. Sulfate by-products in the product solution, are undesirable because of the potential formation damage caused by precipitation of $CaSO_4$ and/or $BaSO_4$, and in addition can be metabolized by sulfate-reducing bacteria to produce corrosive "souring", gas $H_2S$. Some methods of preparation have resulted in sludges, objectionable due to potential clogging of the oil-bearing strata.

Aqueous solutions of sulfate-free propionate-sequestered chromium(III) of good clarity, easily and readily prepared in a reproducible manner have been a goal, or perhaps an obstacle, in the path of the use of this highly important material in oil field processes.

BRIEF DESCRIPTION OF THE INVENTION

We have discovered a unique process in which the use of an inorganic sulfur compound reducing agent such as bisulfite and a chromium(VI) oxidant such as a chromate or dichromate in admixture with a propionic acid source, and water, employing particular proportions and separatory steps, results consistently in a two liquid phase system of which one is an easily separable essentially sulfate-free clean clear green chromium(III) propionate solution, a propionate-sequestered chromium(III).

Our method of producing a clear clean green propionate-sequestered chromium(III) solution involves two basic steps:
(a) reduction of $Cr^{+6} \rightarrow Cr^{+3}$ by, e.g., bisulfite in aqueous propionic acid,
(b) separation of the by-product sulfate-containing phase.

The above steps optionally can be followed by:
(c) dilution and/or neutralization of the Cr(III) propionate solution.

The steps in more detail are as follows:
(a) Reduction of chromium(VI) to chromium(III) is effected by an inorganic sulfur-based compound as reducing agent, such as bisulfite, in aqueous propionic acid containing a sufficient complexing amount of propionic acid, but not more than 55 weight percent. This reductive step at controlled temperature results in two readily separable liquid phases. The lower aqueous phase contains the undesirable sulfate. The upper aqueous phase is sulfate-free and consists of an aqueous acidic solution of propionate-sequestered chromium(III).
(b) Separation of the two-liquid phases is carried out by any convenient means. The sulfate-containing phase is discarded, or otherwise treated for recovery. The clean essentially sulfate-free (upper) phase solution of aqueous acidic propionate-sequestered chromium-(III) solution is retained as product for use in downhole treatment.

Subsequently, to the aqueous acidic propionate-sequestered chromium(III) solution, can be added a further acid, other than propionic acid, if desired, or where needed as discussed hereinafter.

The aqueous acidic propionate-sequestered chromium(III) solution, with the additional acid where employed, can be diluted with water to a convenient metering volume, or partially neutralyzed with an alkaline agent, or both, in any order.

At least about a 4:1 molar ratio of propionate:chromium is required to ensure a proper chromium(III) propionate solution and further that an excess of acid (ligand) is necessary to form a stable solution so as to have a total ligand:chromium molar ratio on the order of at least about 11:1. This needed excess ligand acidity can be provided by a less expensive acid than propionic acid, such as acetic acid or muriatic acid, if such other acid is added after the chromium(III) propionate complex solution itself is first formed, and thus achieve a stable solution at lesser cost.

It is an object of our invention to prepare propionate-sequestered chromium(III) solutions of effective character, uniform, clear, essentially sulfate-free, and without sludge or polymer content. It is a further object of our invention to prepare chromium(III) propionate solutions useful for gelling water-soluble polymeric viscosifiers. It is also an object of our invention to provide improved methods of permeability contrast correction in high permeability streaks both for indepth cross-linking applications and for near-well applications. An additional object of our invention is to provide a method to produce propionate-sequestered chromium-(III) solutions in a stable as well as an economical form. It is also an object of our invention to provide a method for treating underground formations employing a gelable injectable liquid composition employing our propionate-sequestered chromium(III) solutions.

Figure 1:
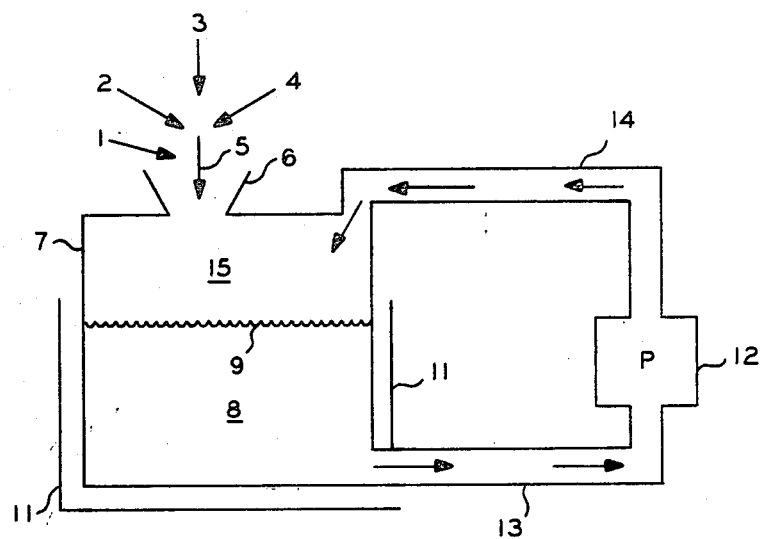
FIG. 1 illustrates a preferred method of mixing the preparative ingredients to form the solution of the chromium(III) propionate-sequestered complex. Chromium(VI) compound 1, sulfite-type reducing agent 2, acid 3, and water 4, are added 5 through opening 6 to mixing vessel 7 to form admixture 8, will fill or level line shown as 9. Heating/cooling 11 controls mixture temperature. Loop circulating pump 12 provides mixing by taking admixture out 13 and returning 14. A free-board 15 is maintained to avoid overfilling and splash-out. After desired mixing, the mixture can be allowed to separate, or can be transferred to a separatory means.

Spectrum (1) is that of a solution prepared with the reaction system of dichromate, nitrite and aqueous propionic acid.

Spectrum (2) is that of a solution made according to the present invention resulting from the reaction system of dichromate, bisulfite and aqueous propionic acid. This solution resulting from our two-phase system is satisfactory.

Spectrum (3) is that of a solution resulting from the reaction system of dichromate, nitrite, aqueous propionic acid and muriatic acid.

Spectrum (4) is that of a solution resulting from the reaction system of chromium(III) nitrate, aqueous propionic acid and propionic anhydride. It would appear chemically satisfactory, except that the high cost of the chromium(III) nitrate makes it unattractive on a commercial basis.

Spectrum (5) is that of a solution resulting from the reaction system of potassium dichromate, propanal, and aqueous propionic acid. This solution is unsatisfactory for gelling polymers in permeability contrast correction operations.

DETAILED DESCRIPTION OF THE INVENTION

In producing the propionate-sequestered chromium-(III) solutions in accordance with our invention, several components are employed: (1) an inorganic sulfur-based compound as reducing component in which the valence of the sulfur is less than +6, (2) a chromium(VI) oxidizing component, (3) a ligand selected from (a) a propionic acid source, and (b) a propionic acid source with an additional acid, and (4) water. Subsequently, preferably, employing (5) an alkaline agent for pH adjustment of the product solution.

CHROMIUM(VI) COMPONENT

The chromium(VI) component is selected from chromium(VI) oxide and the alkali metal and ammonium dichromates and chromates. Presently preferred is sodium dichromate dihydrate for availability and economy. There is no particular difference whether the chromium(VI) component is chromate or dichromate, since in acidic solutions the chromate in any event is converted to dichromate. Whenever chromate is employed, then additional amounts of the propionic acid source are required accordingly and are readily calculated.

REDUCING COMPONENT

The inorganic sulfur-based compound as reducing component can be generically termed a sulfite-type, and is selected from inorganic sulfur compounds in which the valence of sulfur is less than +6, such as sulfur dioxide, and the alkali metal and ammonium salts of hydrosulfites (hyposulfites), dithionites, sulfites including bisulfites, and pyrosulfites (metabisulfites); presently preferred is sodium sulfite or sodium bisulfite for availability and economy. While hydrogen sulfide would be operable, the hazards involved are such that it is not recommended. Sulfur dioxide is less preferred for similar reasons.

PROPIONATE LIGAND SOURCE

The propionate ligand source is selected from propionic acid and propionic acid anhydride. The propionic acid anhydride forms propionic acid upon adequate dilution with water. Mixtures of propionic acid and ammonium or alkali metal propionate are also suitable sources; presently not preferred for economy.

WATER

Water is required to make the admixtures for reduction. In order of preference, suitable water includes demineralized water, zeolite softened water, fresh water, and sodium chloride brine. The water employed should be a clear water, avoiding sediment-containing waters, not so much that such will interfere in the preparation of suitable chromium(III) propionate solutions, but rather that sediments may interfere with the suitability of the stabilized solutions as hereinafter described, and injected solids may provide troublesome formation damage in subterranean strata.

OPTIONAL ADDITIONAL ACIDS

The additional acid component can be selected from any of the mineral acids, acetic acid, acetic anhydride, propionyl halides, and acetyl halides such as acetyl chloride. Mineral acids include such acids as muriatic (hydrochloric) acid, hydrobromic acid, phosphoric acid, and sulfuric acid, including mixtures. Presently, muriatic acid and acetic acid are preferred for convenience, availability, and economy. Sulfuric acid, while technically operable, is to be avoided since it is counter to our invention in that it adds sulfates to the liquor, which are objectionable in connate barium-containing water, and also to some extent objectionable in calcium containing waters, because of the formation in insoluble sulfates. Sulfates also can be metabolized by sulfate-reducing bacteria. Phosphoric acid, while operable, also is less suitable since it is objectionable in calcium-containing connate waters due to the formation of insoluble phosphates.

Acetic acid, phosphoric acid, and sulfuric acid, each can be obtained in varying strengths up to 100 percent. With these, the added acid can be readily calculated. Hydrochloric acid (muriatic acid) is commercially obtainable as a moderately concentrated solution in various grades of 28 to 37 percent hydrochloric acid (hydrogen chloride), so allowance must be made for the additional water involved.

The mixed ligand product is preferred for near-well treatments since it tends to gel the polymer somewhat more quickly, though it is also suitable for indepth crosslinking applications. The higher propionate-containing solutions presently are preferred for indepth crosslinking applications since they tend to take longer to effect gelling of the injected polymer, though they are useful for near-well treatment procedures.

CHROMIUM(VI) REDUCTION

The propionic acid source should be diluted with water in order to form the proper dilute solution found suitable for dissolving the reducing agent and the chromium(VI) source therein for solubility and reactivity and for later separatory purposes.

In acciordance with our method, the step of reduction is conducted in an admixture of water and propionic acid. It is recommended that the acid solution contain in the range of about 9 to 55 weight percent propionic acid (molar ratio of water to propionic acid varies over the range of about 41.7:1 to 3.4:1), preferably about 30 to 50 weight percent propionic acid (molar ratio of water to propionic acid varies over the range of about 9.6:1 to 4.1:1) and definitely not more than about 55 weight percent propionic acid (molar ratio of water to propionic acid is about 3.4:1). By this control of acid concentration, the reduction step results in the formation of two distinct liquid phases.

If the aqueous acid solution contains more than 55 weight percent propionic acid, then a single phase forms, and the resulting solution of propionate sequestered chromium(III) is contaminated with by-product sulfate.

It requires at least about a 4:1 molar ratio of propionate:chromium(III) to ensure the preparation of a suitable chromium(III) propionate solution. Preferably, the total acid ligand:chromium(III) molar ratio should be on the order of at least about 11:1. This preferred total acid ligand level can be provided entirely by propionic acid, or in part thereby so long as the minimum 4:1 molar ratio of propionic acid:chromium(III) is employed initially. The balance of the excess acidity can be a less expensive acid if added after the propionate-sequestered chromium(III) solution is formed, thus achieving a stable solution at lesser cost.

The sequence of adding reactants should be followed with care. In general, the propionic acid source is first diluted with sufficient water to form the recommended concentration of propionic acid. The chromium(VI) source is added with stirring until solution is complete. Heating can be applied as necessary in order to facilitate solution.

Thereafter, the calculated amount of the reducing agent based on the amount of chromium(VI) source employed is added, slowly, with stirring, at an addition temperature of not over about 70° C.

Sufficient reducing component is employed so as to reduce the chromium(VI) source completely to chromium(III). Preferably, at least a small stoichiometric excess of reducing agent source is employed relative to the chromium(VI) source. The amount or ratio of reducing agent depends on the sulfur compound chosen and its reducing capability vis-a-vis Cr(VI)→Cr(III). For example, with sulfite, a molar ratio of at least about 3:1 sulfite:dichromate is recommended. Presently preferred is a molar ratio of sulfite:dichromate of about 3.1:1 to 3.5:1. Excess sulfite above this level is objectionable since an essentially sulfate-free preparation is desired. The slight stoichiometric excesses required for other of what we term generically the sulfite-type of reducing agents can be readily calculated.

Sufficient of the chosen sulfite-type reducing agent must be employed so as to ensure the complete reduction of chromium(VI), since residual dichromate is detrimental to polymer gel stability in applications wherein the chromium(III) propionate solution is used to gel polymers for permeability contrast correction in enhanced oil recovery operations.

After the reactants/reagents have been admixed together in the reduction step, a sufficient effective time and temperature should be allowed to provide a suitable digestion reaction to produce the desired chromium(III) propionate solution. The digestion/reduction temperature employed should be controlled so as to avoid excessively high reaction temperatures. Presently suggested are reaction times with stirring on the order of about 0.5 to 24 hours, presently preferred about 1 to 4 hours; and reaction temperatures of about 40° C. to 100° C., presently preferred about 70° C. to 90° C.

There seems to be a relationship between a need for longer reaction times at lower reaction temperatures, particularly at the lower end of the reactant concentration ranges, whereas somewhat lower reaction temperatures and shorter reaction times are suitable for somewhat higher reactant concentrations. In general, the digestion period needed is shorter at the upper end of the reaction temperature range, as might be expected in most chemical reactions. It should be noted that times greater than 24 hours can be employed for reaction or digestion, though such are not necessary since the reactions generally are essentially complete within 24 hours at reasonable temperatures within the designated reaction temperature ranges and at reasonable or practical concentrations within the designated molar ratio ranges of reactants.

The loop reactor means shown in FIG. 1 and described hereinabove is useful in that it tends to reduce sharply the time of digestion, frequently by up to 50 percent.

SEPARATION

After completion of the reduction and digestion, the admixture is permitted to settle and separate.

By employing our method of controlled acid-water proportions, the resulting admixture after the oxidation-reduction reaction separates cleanly into two liquid phases.

The lower phase is an aqueous phase containing substantially all of the undesirable by-product sulfate ions. The lower phase is separated and removed, by any convenient separatory technique, and discarded or recycled for sulfate removal and recovery if desired.

The upper phase consists of an aqueous acidic propionate-sequestered chromium(III) solution, and is employable in gelation of aqueous polymers.

The product obtained as the upper phase is an aqueous homogeneous green solution of propionate sequestered cromium(III). With suitable ratios, temperature, and digestion time, there is no residual dichromate and no sediment or brown sludge.

The process/reaction appears to be much more than the mere formation of what might be viewed as a simple chemical compound chromium(III) propionate which conventionally would be considered Cr(propionate)$_3$. Rather, employing reagents, proportions, reaction times, temperatures, as recommended, stable clear green solutions of propionate-sequestered chromium-(III) are obtained which exhibit characteristic visible spectra.

The upper phase can be further treated by dilution and/or neutralization, as may be desired.

DILUTION/PARTIAL NEUTRALIZATION

The retained liquid phase contains (excess) propionic acid and the complex of chromium(III) propionate.

To the admixture can be added water to a more convenient volume. Amounts are not critical. Suggested is about equal volumes of water and aqueous complex.

PARTIAL NEUTRALIZATION

The green solutions of chromium(III) propionate, with or without dilution, are ready for oil-field use. The solutions, however, are particularly acidic if a proportion of the acidity is provided by a strong acid such as muriatic acid. Such solutions may tend to be relatively corrosive to some metals due to the inherent acidity.

The propionate-sequestered chromium(III) solutions preferably are partially neutralized to minimize potential handling hazards and moderate the corrosiveness of these solutions toward lines and pumping equipment.

The pH of the chromium(III) propionate solutions preferably is raised to such as about 3 to 5, more preferably about 3 to 4, by use of an alkaline agent such as ammonia, ammonium hydroxide, or an alkali metal hydroxide such as sodium hydroxide. Alkali metal carbonates can be used, but the effervescence of carbon dioxide poses an obvious handling problem.

The alkaline agent preferably is diluted with water and added slowly with stirring to the chromium(III) propionate solution. The pH can be monitored for control purposes.

FURTHER DILUTION

The resulting partially neutralized chromium(III) propionate solutions can be used as prepared. The as-prepared stable solutions of our invention can be held or stored indefinitely, preferably in closed corrosion-resistant drums.

The stable solutions can be further diluted with water, if desired, so as to provide greater volumes for easier metering and mixing prior to use in water channeling control applications.

Dilution preferably is with soft or fresh water. The extent of dilution can be as convenient, though up to a maximum of about 1 part solution:100 parts water by volume is suggested to avoid possible loss of stability.

Our clear, sulfate-free, aqueous propionate-sequestered chromium(III) solutions are useful for gelling polymeric viscosifiers such as polyacrylamide solutions, for example, the sequential injection of polyacrylamide-brine-chromium(III) propionate-brine-polyacrylamide, in use in such as Berea sandstone, and useful even in the presence of hard brines such as South Burbank Unit brine, and are useful in the development of high residual resistance factors (RRF).

EXAMPLES

Examples provided are intended to assist one skilled in the art to a further understanding of our invention. Particular materials employed should be considered as exemplary and not limitative. The Example is part of our disclosure. The specification including text, Example, data, and claims, should be viewed as a whole in considering the reasonable and proper scope of our invention.

WORKING EXAMPLE

Experimental runs were carried out on a laboratory scale in a 500 mL glass reactor.

In the laboratory scale runs, a 500 mL 3-necked round-bottomed flask was used. This vessel was equipped with a variable speed mechanical stirrer, a water-cooled reflux condenser and a thermocouple probe for determining the temperature of the reaction mixture. A heating mantle was used as necessary to supply heat to the reactor.

Generally, the aqueous propionic acid was charged to the reactor, and the designated amount of dichromate then added and dissolved at ambient temperature with stirring. Sodium bisulfite then was added in portions either as a solid or as small volume aliquots of an aqueous $NaHSO_3$ solution. The addition was carried out slowly with stirring, and with cooling if necessary so that the temperature of the reaction mixture did not exceed 50° C. After all of the reactants were added, the stirred mixture was heated to a specified temperature for a designated time period.

At the end of the reaction period, the solution was cooled to ambient temperature and checked for residual dichromate and sulfate and/or bisulfite. In the residual dichromate test, a small sample of the reaction mass was contacted with one to two drops of a 0.1M barium chloride solution. The appearance of a yellow-white precipitate signaled the presence of residual dichromate and such a product mixture was considered unacceptable for crosslinking (gelling) polymeric viscosifier, such as polyacrylamides, in enhanced oil recovery operations. Residual dichromate in such gels can cause polymer degradation. The formation of a white precipitate indicated the presence of sulfate and/or bisulfite.

The reaction mixture also was checked for the presence of water-insoluble polymeric species. The exact chemical nature of these species is not known, though such species may be polymeric aggregates containing chromium and propionic acid units. In this test, a small sample of the reaction mass was diluted with distilled water. The appearance of a white film or skin on the surface of the liquid or on the sides of the beaker signaled the presence of polymeric species. The appearance of this water-insoluble material rendered the product mixture unacceptable for use in enhanced oil recovery operations because the presence of insolubles would give rise to injectivity problems.

Figure 2:
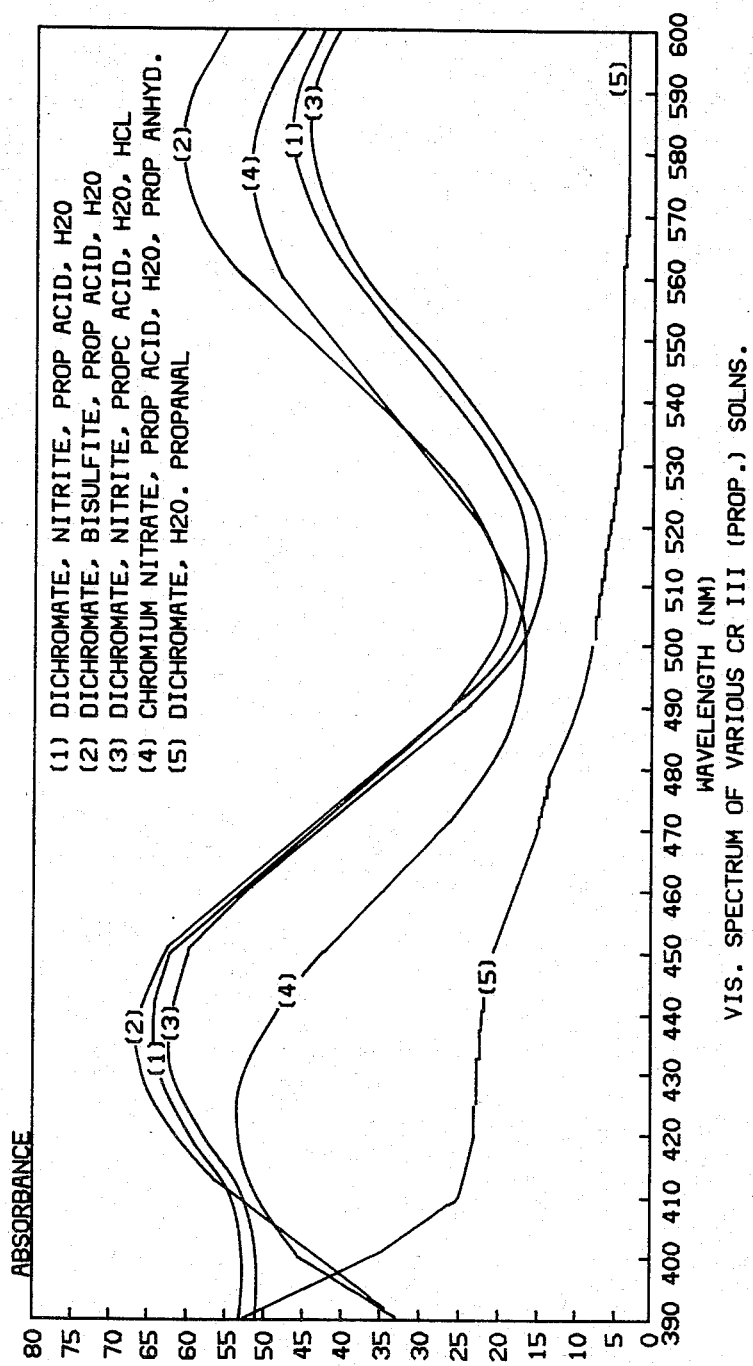
FIG. 2 presents the spectra of solutions of material resulting from several different preparative routes for the attempted preparation of active chromium(III) propionate solutions. The spectra are shown in the visible range of 390 to 600 nm wavelength numbers. Active chromium(III) propionate solutions exhibit absorbance maxima at about 435 nm and 580 nm.

The reaction mass also was characterized by visible spectral analysis. A sample was scanned over the visible spectrum between 390 nm and 600 nm on a Perkin Elmer 530 UV-Visible Spectrophotometer. Samples which were clear and green and which exhibited maximum absorbance peaks at 435 nm and 580 nm were considered to be suitable for crosslinking (gelling) polymeric viscosifiers for use in enhanced oil recovery operations. See FIG. 2 herewith.

In this work, samples of the reaction mass were checked for the presence of residual dichromate, water-insoluble polymeric species and characterized by visible analysis before any bulk gels or core tests were carried out. Suitable product masses were transparent, dark green-colored solutions which contained no solids and no solids were produced on dilution of these mixtures with water.

EXAMPLE I

This Example presents typical laboratory scale runs which produced "active" chromium(III) propionate solutions.

Preparative laboratory runs are summarized in Table I:

TABLE I

Bisulfite/Dichromate Redox System in Aqueous Propionic Acid for Preparation of Sulfate-Free Chromium (III) Propionate Solutions

| Run No. | Approximate Weight Ratio $CH_3CH_2CO_2H/H_2O$ | Reaction Conditions Total Time (Hrs.) | (°C.) | Remarks |
|---|---|---|---|---|
| 1 | 47/53 | 3.5 | 70 | (a) |
| 2 | 47/53 | 5 | 70 | (a) |
| 3 | 44/56 | 3 | 70 | (a) |
| 4 | 38/62 | 3 | 70 | (a) |
| 5 | 44/56 | 3 | 70 | (a) |
| 6 | 44/56 | 1.5 | 90 | (b) |
| 7 | 44/56 | 2 | 90 | (b) |
| 8 | 44/56 | 3 | 90 | (b) |
| 9 | 44/56 | 2 | 90 | (b) |
| 10 | 83/17 | 4 | 70 | (c) |

(a)Increments of water and propionic acid were added to reach the weight ratios shown.
(b)reactants were present in the original mixture.
(c)Incremental amounts of propionic acid were added to reach the weight ratio shown. Two phases did not form in this Run 10.

Each of Runs 1-9 gave an upper phase green-colored transparent solution. The upper phase was free of sulfate, whereas the lower phase was rich in sulfate.

Referring to the results summarized in Table I, attention is called to Runs 1, 2, 3, 4 and 5 which demonstrate that at 70° C., that a digestion period of 3 to 5 hours is sufficient and effective to prepare the chromium(III) propionate solution, whereas Runs 6, 7, and 9 demonstrate that at 90° C., a digestion period of only 1.5 to 2 hours is sufficient. These product solutions contained no residual dichromate and produced no insoluble material on dilution with water. The visible spectra of these "active" solutions exhibited absorbance maxima at 435 nm and 580 nm.

POLYMERS

Polymers suitable for use with the propionate-complexed chromium(III) solutions of our invention are those capable of gelling in the presence of polyvalent metal ion crosslinking agents within a gelation pH range. Polymers suitable for use in this invention, i.e., those capable of gelling in the presence of crosslinking agents within a gelation pH range, include biopolysaccharides, cellulose ethers, and the acrylamide-based polymers. These should be polyanionic wherein at least a portion of the anionic sites should be carboxylate and/or carboxylic acid groups.

Suitable polymers preferably have pendant carboxylate groups

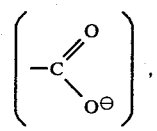

or, also preferably, carboxylic acid groups

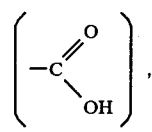

which provide sites for crosslinking with polyvalent metal cations such as chromium(III) available, e.g., from the dissociation of $Cr^{+3}$ from sequestered chromium in chromium(III) propionate.

Biopolysaccharides possess "natural" sites for crosslinking such as oxygen-containing functional groups such as —OH and possibly —$CO_2H$. Cellulose ether-based polymers likewise preferably contain pendant anionic sites such as in carboxymethyl cellulose (CMC) to be effective for crosslinking, viz., —$CH_2CO_2^-$.

Theoretically, one would not expect a completely nonionic polymer to crosslink, i.e.:

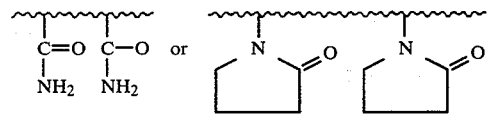

since, e.g., there are no carboxylate or carboxylic acid or other groups such as —OH present for crosslinking.

In general, there are two primary methods to prepare "crosslinkable" polymer, e.g. (1) The hydrolysis of functional groups to generate carboxylate or carboxylic acid groups and (2) the polymerization of monomers at least one of which bears a carboxylate or carboxylic acid group:

(1) Partial hydrolysis of functional groups on a polymer substrate can give rise to carboxylate (pH >7) or carboxylic acid sites (pH <7), e.g.:

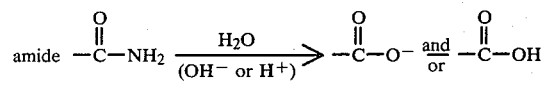

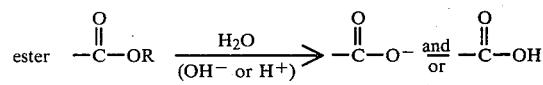

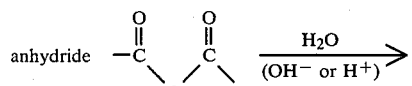

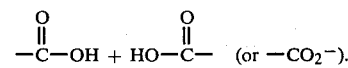

For example, a

50/50 poly(N—vinyl-2-pyrrolidone-co-acrylamide) copolymer (VP/Am)

↓ H₂O (aging) (OH⁻ or H⁺)

poly(N—vinyl-2-pyrrolidone-co-acrylamide-co-acrylic acid) (VP/Am/AA) or (VP/Am/NaAA).

However, such aging can require a long period of time, which is commercially desirable.

(2) Polymerization of monomers at least one of which possesses a carboxylic acid or carboxylate moiety:

A monomer such as sodium acrylate is used in the polymerization to prepare acrylate modified polymer directly, e.g., the terpolymerization of N-vinyl-2-pyrrolidone, acrylamide, and sodium acrylate would yield poly(N-vinyl-2-pyrrolidone-co-acrylamide-co-sodium acrylate)(VP/Am/NaAA).

Suitable crosslinkable cellulose ethers include those disclosed in U.S. Pat. No. 3,727,688 (incorporated herein by reference). Particularly preferred cellulose ethers include carboxymethylhydroxyethyl cellulose (CMHEC) and carboxymethyl cellulose (CMC). Each of these cellulosic ether polymers possess pendant carboxymethyl groups ($-CH_2CO_2^-$) introduced, e.g., by the carboxymethylation of cellulosic $-OH$ groups with chloroacetic acid under alkaline conditions as is well known in the art.

Suitable biopolysaccharides include those disclosed in U.S. Pat. No. 4,068,714 (incorporated herein by reference). Particularly preferred of these is polysaccharide B-1459, a biopolysaccharide produced by the action of *Xanthomonas campestris* bacteria, and commercially available in various grades under the trademark Kelzan ® (Kelco Company, Los Angeles, Calif.).

Among the suitable acrylamide-based polymers are those disclosed in U.S. Pat. No. 3,749,172 (incorporated herein by reference). Particularly preferred are the so-called partially hydrolyzed acrylamide-based polymers possessing pendant carboxylate groups through which crosslinking can take place. Thermally stable copolymers of acrylamide, such as poly(N-vinyl-2-pyrrolidone-co-acrylamide) and poly(sodium 2-acrylamido-2-methyl-1-propanesulfonate-co-acrylamide), are particularly preferred for applications in high salinity environments at elevated temperatures. Selected terpolymers also are useful in the present process, such as terpolymers derived from acrylamide and N-vinyl-2-pyrrolidone comonomers with lesser amounts of termonomers such as acrylic acid, sodium acrylate, vinyl acetate, vinylpyridine, styrene, methyl methacrylate, and the like. Sodium acrylate modified acrylamide-based polymers such as poly(N-vinyl-2-pyrrolidone-co-acrylamide-co-sodium 2-acrylamido-2-methyl-1-propanesulfonate-co-sodium acrylate)(30/10/55/5 wt/wt/wt/wt) are particularly preferred.

Other miscellaneous polymers suitable for use in the present invention include partially hydrolyzed polyacrylonitrile, polystyrene sulfonate, lignosulfonates, methylolated polyacrylamides, and the like.

In general, the gelation pH range is a pH range of about 1 to 12 preferrably about 3 to 7. It is recognized that this range may vary somewhat for various polymers, or polymer-metal cation combinations or concentration relationships. The specific gelation pH range is readily determinable for a given or specific polymer or polymer-metal cation combination by testing same with additions of acid or base and following the resulting pH change until gelation is observed.

Presently preferred are the acrylamide based polymers, particularly the polyacrylamides and the partially hydrolyzed polyacrylamides, preferably in conjunction with $Cr^{3+}$ as the metal cation, presently most preferably as the instant chromium(III) propionate solution.

The concentration or water-thickening amount of the water-soluble/dispersible polymer in the aqueous solution/dispersion can range widely and be as suitable and convenient for the various polymers, and for the degree of gelation needed for particular strata. Generally, the concentration of polymer in its aqueous solution/dispersion (before admixing with crosslinking components or ester) is about 100 to 20,000 ppm, preferably about 200 to 10,000 ppm.

Any suitable procedures for preparing the aqueous admixtures of the crosslinking polymer can be used. Some of the polymers may require particular mixing conditions, such as slow addition of finely powdered polymer into the vortex of stirred water, alcohol pre-wetting, protection from air (oxygen), preparation of stock solutions from fresh rather than salt water, or the like, as is known for such polymers.

Generally, the ratio of number of polyvalent metal cations to crosslinkable side groups on the polymeric viscosifier will vary over the broad range of about 10:1 to 1:10, presently preferably about 5:1 to 1:1.

Conveniently, the polymer can be dispersed in a given amount of water, and to the dispersion then added the desired amounts of a solution or dispersion of the sequestered polyvalent metal cation crosslinking agent.

After admixing with the aqueous solution of the crosslinking agent, the polymer concentration generally will be of the order of about 200 to 20,000 ppm, more usually about 500 to 5,000 ppm.

COMPOSITIONS FOR INJECTION

The amount of crosslinking agent used depends largely on the amounts of polymer in solution. Lesser amounts of polymer require lesser amounts of crosslinking agent, and vice-versa. Further, it has been found that for a given concentration of polymer that increasing the amount of crosslinking agent generally substantially increases the formation plugging effectiveness.

The chromium(III) propionate solution and the polymer solution can be pre-mixed on the surface and then injected as a slug. The solutions can be kept separate and can be mixed together by inter-mixing devices or valves as injection proceeds, where desired. Alternatively, a sequential injection of aqueous polymer-aqueous chromium(III) propionate-aqueous polymer can also be used for permeability contrast correction.

PREFLUSH (OPTIONAL)

Prior to employment of the gelable compositions, the strata can be subjected to a conditioning preflush step.

The optional preflush employs aqueous solution with a lower level of hardness and/or total dissolved solids (tds) than that of the stratum connate water, of preferably containing substantially no hardness cations though it may be saline. The purpose of the preflush is to alter the salinity of the connate water by flushing the formation, generally with about one to three times the pore volume of the zone to be treated.

Since it is known that enhanced oil recovery chemicals such as surfactants and polymeric viscosifiers are adsorbed and/or precipitated to a greater extent in the presence of electrolytes and hardness cations in particular, the preflush alleviates this potential problem by sweeping out a certain fraction of such electrolytes. A typical NaCl preflush brine contains, e.g., on the order of about 0.2 to 2 weight percent total dissolved solids.

SPACER SOLUTION

Optionally, a spacer solution of a sequestrant can be employed, inbetween the aqueous polymer-aqueous chromium propionate-aqueous polymer sequential repeating cycle, with or without brine spaces. The sequestrant solution preferably is aqueous sodium propionate, but can be an aqueous alkaline metal salt solution of a sequestering anion such as citrate, acetate, tartrate, gluconate, nitriloacetate, any of the polyphosphates of sequestering character, ethylenediaminetetraacetic acid, alone, in admixture, or in admixture with propionate. The spacer sequestrant concentration can be as convenient depending on water solubility. The volume of spacer solution employed can be similar to the suggested amount of preflush employed.

AQUEOUS DRIVE FLUID

The aqueous drive generally follows the permeability contrast correction process of my invention. The aqueous drive employs available field brines and/or fresh water if the latter is obtainable.

The aqueous drive, since it follows our gelation treatment, is diverted to the (formerly) relatively less permeable oil-rich zones since the permeability contrast correction process shows or substantially prevents the flow of aqueous drive fluid through the (originally) more permeable but oil-poor zones (so-called thief zones). A successful permeability contrast correction operation generally is signaled at the production well by a lowering of the water/oil ratio in the produced fluid.

Subsequent to the permeability contrast correction, the water/oil ratio may gradually increase again after prolonged injection of the drive water. A gelation retreatment of the formation may be considered appropriate, if desired.

The disclosure, including data, has illustrated the value and effectiveness of our invention. The Examples, the knowledge and background of the field of the invention and the general principles of chemistry and of other applicable sciences have formed the bases from which the broad descriptions of our invention including the ranges of conditions and the generic groups of operant components have been developed, and formed the bases for our claims here appended.

We claim:

1. A method of producing a two phase liquid system wherein one phase is a stabilized chromium(III) propionate solution and the other phase is a sulfate-containing solution which comprises the steps of:
   (a) admixing a propionic acid source selected from propionic acid and propionic anhydride with water thereby forming an aqueous solution of propionic acid containing about 9 to 55 weight percent propionic acid;
   (b) adding to said aqueous propionic acid a chromium(VI) source selected from the group consisting of chromium(VI) oxide and alkali metal and ammonium dichromates and chromates thereby forming a solution of said chromium(VI) source in said aqueous propionic acid employing a molar ratio of at least about 4:1 propionic acid:chromium;
   (c) adding to said solution of chromium(VI) source in aqueous propionic acid, an inorganic sulfur-based compound as reducing agent wherein the valence of the sulfur is less than six, employing sufficient reducing agent, time and temperature to effectively reduce chromium(VI) to chromium(III) and simultaneously oxidize the reducing agent to sulfate and
   (d) separating said two phase liquid system into a sulfate-containing phase and a chromium(III) propionate-containing phase.

2. The process according to claim 1 wherein said chromium(VI) source is potassium dichromate.

3. The process according to claim 2 wherein said sulfur-based reducing agent is sodium sulfite or bisulfite.

4. The process according to claim 3 wherein said propionic acid propionate source is propionic acid.

5. The process according to claim 1 wherein subsequent to said step (d) an additional acid selected from hydrochloric acid, acetic acid and propionic acid is added to said chromium(III) propionate-containing phase.

6. The process of claim 5 wherein said additional acid is hydrochloric acid.

7. The process of claim 5 wherein said additional acid is acetic acid.

8. The process of claim 1 employing in said step (b) propionic acid in a molar ratio range of about 4:1 to 45:1 propionic acid:chromium.

9. The process of claim 1 employing in said step (b) propionic acid in a molar ratio of at least about 4:1 propionic acid:chromium and subsequent to step (d) an additional acid selected from the group consisting of hydrochloric acid and acetic acid is added to said chromium(III) propionate-containing phase to bring total acidity to at least about an 11:1 molar ratio of acid:chromium.

10. The process of claim 1 employing a reaction time of about 0.5 to 24 hours, and a reaction temperature of about 40° C. to 100° C.

11. The stabilized chromium(III) propionate solution prepared by the process which comprises the steps of:
   (a) admixing a propionic acid source selected from the group consisting of propionic acid and propionic anhydride with water thereby forming an aqueous propionic acid solution containing 9 to 55 weight percent propionic acid;
   (b) adding to said aqueous propionic acid a chromium(VI) source selected from the group consisting of chromium(VI) oxide and alkali metal and ammonium dichromates and chromates thereby forming a solution of said chromium(VI) source in said aqueous propionic acid employing a molar ratio of at least 4:1 propionic acid:chromium;
   (c) adding to said solution of chromium(VI) source in aqueous propionic acid, an inorganic sulfur-based compound as reducing agent selected from the group consisting of alkali metal and ammonium bisulfites, sulfites, pyrosulfites, hydrosulfites and dithionites employing sufficient reducing agent, time and temperature to effectively reduce chromium(VI) to chromium(III) and simultaneously oxidize said reducing agent to sulfate thereby forming a sulfate-containing phase and a chromium(III) propionate-containing phase,
   (d) separating said phases and
   (e) further adding additional acid to said chromium(III) propionate-containing phase to adjust total acidity to at least about an 11:1 molar ratio of acid:- chromium wherein said additional acid is selected from the group consisting of hydrochloric acid, acetic acid, propionic acid and mixtures.

12. The stabilized chromium(III) propionate solution of claim 11 wherein said chromium(VI) source is sodium dichromate.

13. The stabilized chromium(III) propionate solution of claim 12 wherein said reducing agent is sodium bisulfite or sulfite.

14. The stabilized chromium(III) propionate solution of claim 13 wherein said propionic acid source is propionic acid.

15. The stabilized chromium(III) propionate solution of claim 14 wherein said additional acid is hydrochloric acid.

16. The stabilized chromium(III) propionate solution of claim 14 wherein said additional acid is acetic acid.

17. The stabilized chromium(III) propionate solution of claim 14 wherein said additional acid is propionic acid.

18. The stabilized chromium(III) propionate solution of claim 11 employing in said step (b) propionic acid in a molar ratio range of about 4:1 to 45:1 propionic acid:chromium.

19. The stabilized chromium(III) propionate solution of claim 11 employing in said step (b) propionic acid in a molar ratio of at least about 4:1 propionic acid:chromium, and in step (c) a further acid, selected from hydrochloric acid and acetic acid, to bring the total acidity to at least about an 11:1 molar ratio of acid:chromium.

20. The process according to claim 11 employing a reaction time of about 0.5 to 24 hours and a reaction temperature of about 40° C. to 100° C.

* * * * *